United States Patent
Konno

(10) Patent No.: US 11,086,499 B2
(45) Date of Patent: Aug. 10, 2021

(54) PORTABLE INFORMATION TERMINAL, BIOLOGICAL INFORMATION MANAGEMENT METHOD, BIOLOGICAL INFORMATION MANAGEMENT PROGRAM AND COMPUTER-READABLE STORAGE MEDIUM

(71) Applicant: NIHON KOHDEN CORPORATION, Tokorozawa (JP)

(72) Inventor: Norihito Konno, Tokyo (JP)

(73) Assignee: Nihon Kohden Corporation, Tokorozawa (JP)

( * ) Notice: Subject to any disclaimer, the term of this patent is extended or adjusted under 35 U.S.C. 154(b) by 0 days.

(21) Appl. No.: 16/360,899

(22) Filed: Mar. 21, 2019

(65) Prior Publication Data
US 2019/0294319 A1    Sep. 26, 2019

(30) Foreign Application Priority Data
Mar. 23, 2018    (JP) .............................. JP2018-056604

(51) Int. Cl.
*G06F 3/0484*    (2013.01)
*G06F 3/0488*    (2013.01)
*A61B 5/00*    (2006.01)

(52) U.S. Cl.
CPC ........ *G06F 3/04845* (2013.01); *A61B 5/0002* (2013.01); *A61B 5/743* (2013.01); *A61B 5/7475* (2013.01); *G06F 3/04883* (2013.01); *G06F 2203/04803* (2013.01); *G06F 2203/04806* (2013.01); *G06F 2203/04808* (2013.01)

(58) Field of Classification Search
CPC ..... G06F 3/04845; A61B 5/002; A61B 5/743; A61B 5/7475
See application file for complete search history.

(56) References Cited

U.S. PATENT DOCUMENTS

| | | | | |
|---|---|---|---|---|
| 9,665,264 | B1* | 5/2017 | Janiak | G06F 3/017 |
| 2012/0078647 | A1* | 3/2012 | Grassle | G16H 40/67 705/2 |
| 2013/0083222 | A1* | 4/2013 | Matsuzawa | H04N 5/23296 348/240.3 |
| 2013/0271469 | A1* | 10/2013 | Moore | G06T 11/206 345/440.1 |
| 2014/0019901 | A1* | 1/2014 | Powell | A61B 5/044 715/771 |
| 2014/0351738 | A1* | 11/2014 | Kokovidis | A61B 5/7445 715/771 |
| 2015/0243040 | A1* | 8/2015 | Ben-Oni | G06T 11/206 345/629 |

FOREIGN PATENT DOCUMENTS

JP    2015521308 A    7/2015

* cited by examiner

*Primary Examiner* — Roland J Casillas
(74) *Attorney, Agent, or Firm* — Dorsey & Whitney LLP

(57) ABSTRACT

To assist work of checking information by a user when biological information is displayed in a relatively small display area of a portable information terminal. A portable information terminal receives sensor signals corresponding to biological information of a subject from sensors attached to the subject. Waveforms indicating variations with time in biological information of the subject are displayed on a display based on the sensor signals. When a user interface receives a given operation, part of the waveform displayed on the display is designated and a trimmed image of the part of the waveform is displayed on the display.

16 Claims, 5 Drawing Sheets

FIG. 3A
FIG. 3B
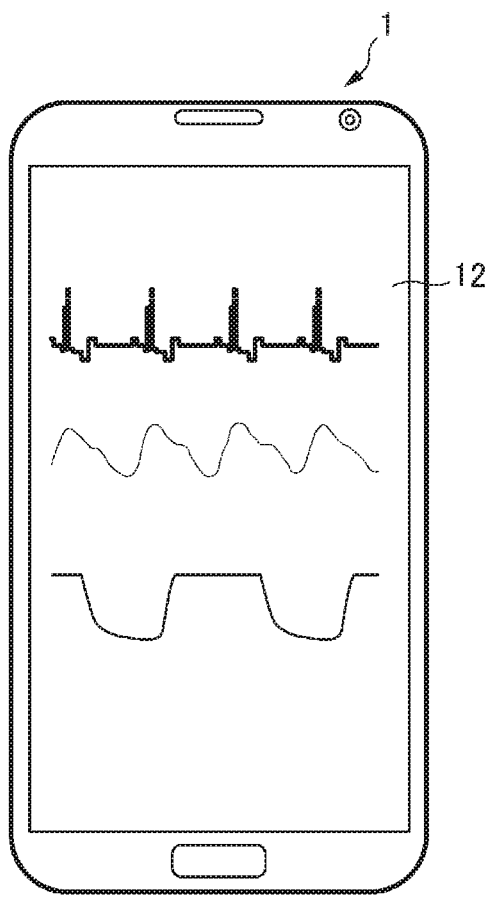
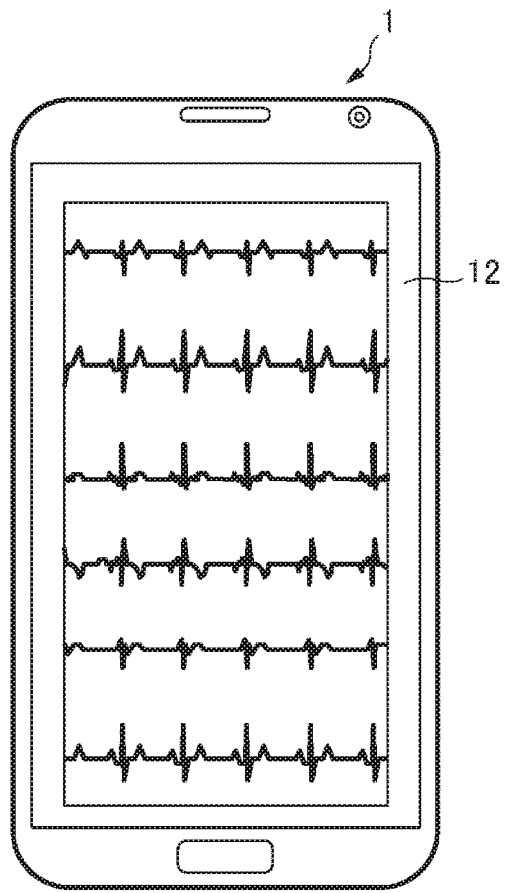

FIG. 4A
FIG. 4B
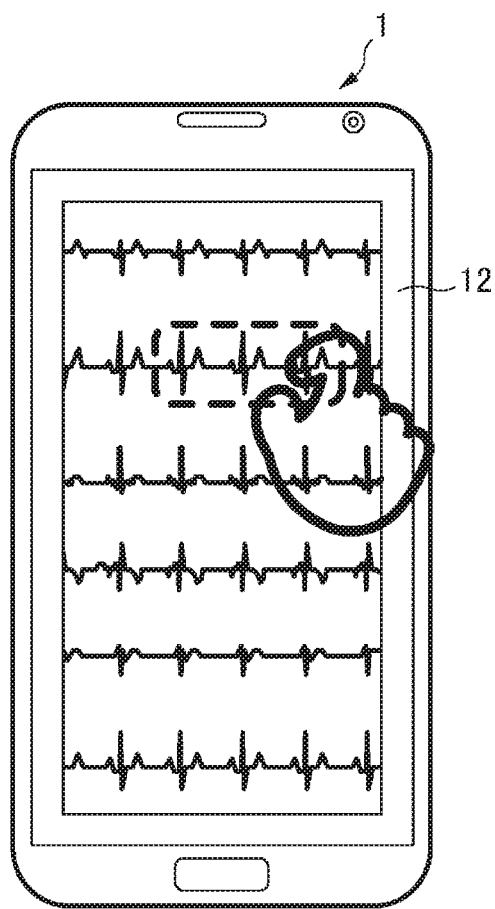
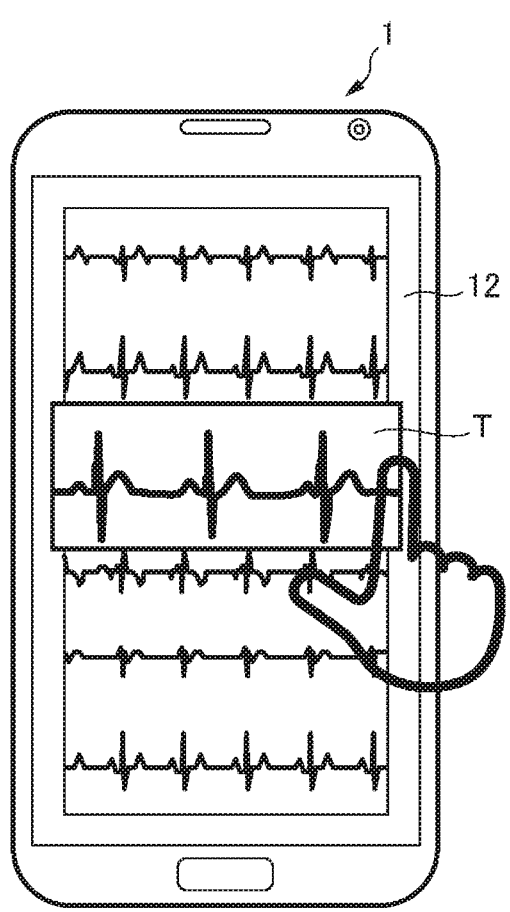

PORTABLE INFORMATION TERMINAL, BIOLOGICAL INFORMATION MANAGEMENT METHOD, BIOLOGICAL INFORMATION MANAGEMENT PROGRAM AND COMPUTER-READABLE STORAGE MEDIUM

CROSS-REFERENCE TO RELATED APPLICATION(S)

This application claims priority to and the benefit under 35 U.S.C. § 119(a) of the earlier filing date of Japanese Application No. JP 2018-056604 filed Mar. 23, 2018 which is incorporated herein by reference, in its entirety, for any purpose.

BACKGROUND OF THE INVENTION

Field of the Invention

The present disclosure relates to a portable information terminal and a biological information management method for managing biological information of subjects, a biological information management program allowing the portable information terminal to execute the biological information management method and a computer-readable storage medium storing the biological information management program.

Description of Related Art

There is a demand for checking biological information of subjects on a portable information terminal. A configuration described in JP-A-2015-521308 (Patent Literature 1) has been made for meeting the demand.

SUMMARY OF THE INVENTION

An object of the present disclosure is to support work of checking information by a user when biological information is displayed in a relatively small display area of a portable information terminal.

In order to achieve the above object, a portable information terminal according to an embodiment includes a wireless communication device receiving sensor signals corresponding to biological information of a subject, a display displaying waveforms indicating variations with time in biological information of the subject based on the sensor signals, and a user interface receiving a given operation, in which, when part of the waveform is designated by the given operation, a trimmed image of the part of the waveform is displayed on the display.

BRIEF DESCRIPTION OF THE DRAWINGS

FIGS. 3A and 3B show display examples on a display of the above portable information terminal;

FIGS. 4A and 4B show display examples on the display of the above portable information terminal.

DESCRIPTION OF EMBODIMENTS

Figure 1:
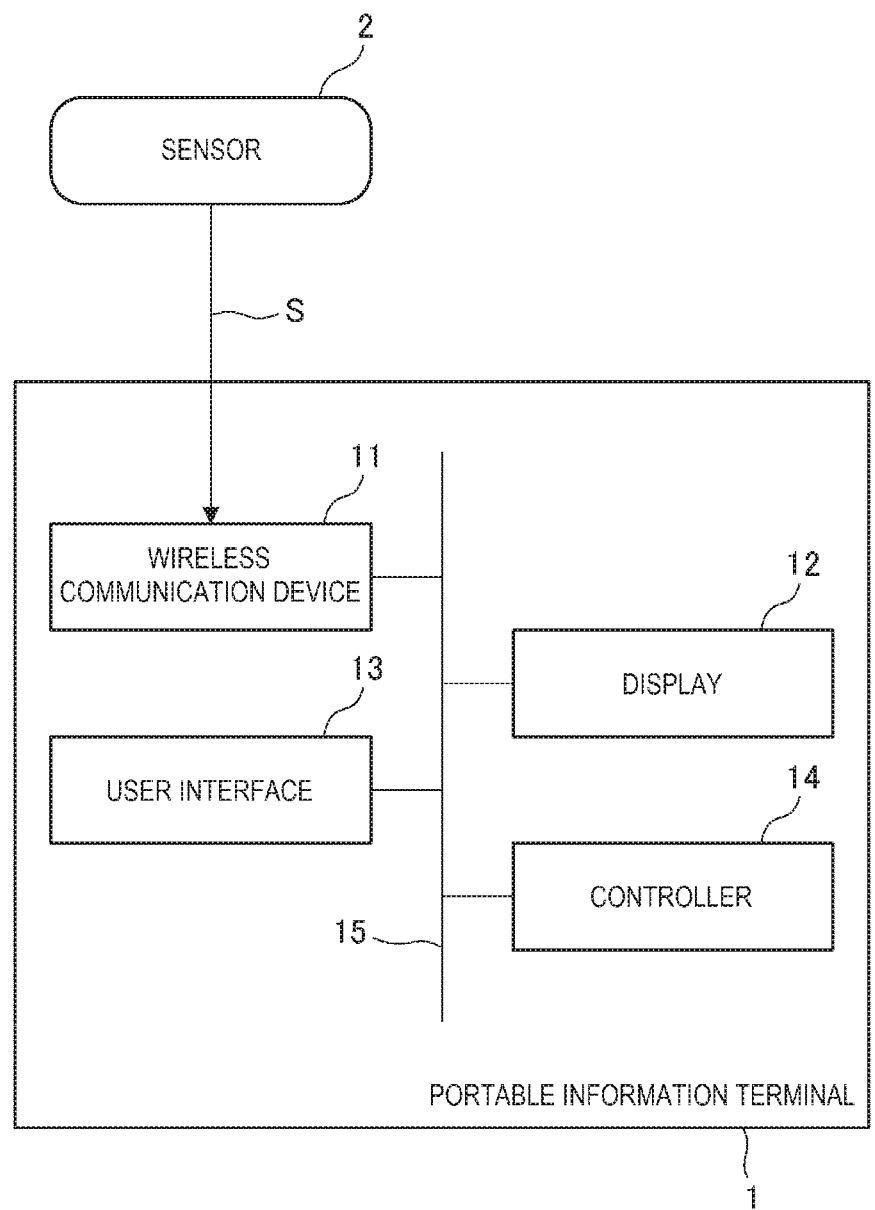
FIG. 1 shows a functional configuration of a portable information terminal according to an embodiment.

Examples of an embodiment will be explained below in detail with reference to the attached drawings. FIG. 1 shows a functional configuration of a portable information terminal 1 according to the embodiment.

The portable information terminal 1 is a portable device having a display function and an information processing function. As the portable information terminal 1, a smart phone, a tablet terminal, a head mount display and so on can be cited as examples. The portable information terminal 1 configures a biological information management system with at least one sensor 2 attached to at least one subject.

The sensor has a configuration in which biological information of a subject is detected and a sensor signal S corresponding to the biological information is outputted. As biological information, a body temperature, a blood pressure, an electrocardiogram, an electromyogram, brain waves, arterial blood oxygen saturation (SpO2), concentration of carbon dioxide or oxygen in respiratory gas, a partial pressure and so on can be cited as examples.

The portable information terminal 1 includes a wireless communication device 11. The wireless communication device 11 includes a communication interface capable of performing wireless communication with the sensor 2. As such interfaces, communication interfaces conforming to standards such as RFID (Radio Frequency Identification), NFC (Near Field Communication), Bluetooth (trademark) and Wi-Fi can be cited as examples. The wireless communication device 11 receives at least one sensor signal S from at least one sensor 2 attached to at least one subject.

The information terminal 1 includes a display 12. The display 12 is configured to display various types of information. As the display 12, a liquid crystal display, an organic EL display device and the like can be cited as examples.

The portable information terminal 1 includes a user interface 13. The user interface 13 is configured to receive given operations from the user. As the user interface 13, physical switches such as buttons or levers, a touch panel device integrated with the display 12 to allow touch input, a voice recognition device receiving input by voice instructions and a line-of-sight recognition device receiving instructions by line-of-sight input can be cited as examples.

The portable information terminal 1 includes a controller 14. The controller 14 includes a processor. The processor is configured to execute at least part of a later-described biological information management method. Functions of the processor may be realized by a general-purpose microprocessor operating in cooperation with a memory, or may be realized by a dedicated integrated circuit such as a microcontroller, FPGA or ASIC.

The portable information terminal 1 includes a communication bus 15. The wireless communication device 11, the display 12, the user interface 13 and the controller 14 can exchange signals and data mutually through the communication bus 15.

Figure 2:
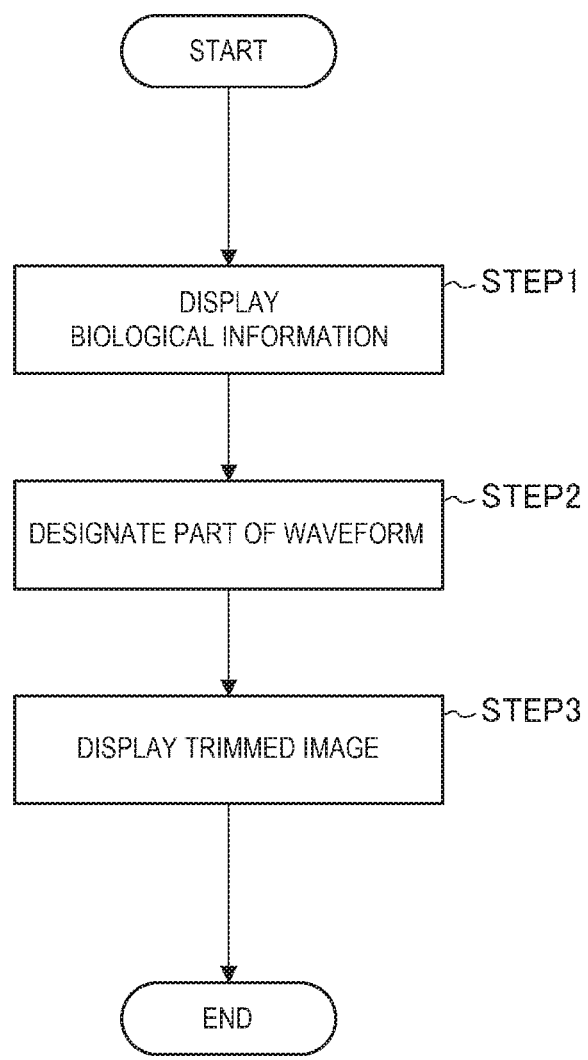
FIG. 2 shows the flow of processing executed by the above portable information terminal.

FIG. 2 shows an example of the biological information management method performed in the portable information terminal 1 configured as described above. Processing executed in the portable information terminal 1 is performed under control of the controller 14.

The portable information terminal 1 displays a waveform indicating variation with time in biological information of a subject on the display 12 based on the sensor signal S received from the sensor 2 attached to the subject (STEP 1).

FIG. 3A shows an example of display modes. In the present example, a plurality of waveforms indicating variations with time in a plural kinds of biological parameters are displayed on the display 12 based on a plurality of sensor signals S received from a plurality of sensors 2 attached to one subject. For example, a waveform indicating variation with time of an electrocardiogram of a single channel, a waveform indicating variation with time of noninvasive arterial blood oxygen saturation and a waveform indicating variation with time of concentration of carbon dioxide in respiratory gas may be displayed.

FIG. 3B shows another example of display modes. In the present example, a plurality of waveforms indicating variations with time of electrocardiograms of plural channels are displayed on the display 12 based on a plurality of sensor signals S received from a plurality of sensors 2 attached to one subject.

It is also preferable that waveforms indicating variations with time of electrocardiograms of single channels of one subject are displayed in a cascade mode over several rows, though not shown. Moreover, waveforms indicating variations with time of at least one biological information for plural subjects may be displayed.

Subsequently, as shown in FIG. 4A, part of the waveform displayed on the display 12 is designated (STEP 2 in FIG. 2). Specifically, part of the waveform is designated through the user interface 13 receiving a given operation. An area selected in the same drawing is surrounded by a broken line.

In the specification, "designation of part of the waveform" means that one area relating to one subject is selected from plural areas in which waveforms relating to plural subjects are displayed, that one waveform is selected from plural waveforms indicating variations with time of plural kinds of biological parameters relating to one subject and that an area including a smaller amount of information than that of biological information originally displayed on the display 12 is designated through designation of part of a waveform indicating variation with time of a specific biological parameter relating to one subject (namely, a specific time range).

As given operations, an operation of a physical switch, touch operation input to a touch input panel, voice instruction input, line-of-sight instruction input and so on can be cited as examples.

As a result, as shown in FIG. 4B, a trimmed image T of the designated part of the waveform is displayed on the display 12 (STEP 3 in FIG. 2). The trimmed image T is provided as an independent display area, which includes image information alone which has been originally displayed in part of the area on the display 12 designated through the user interface 13.

The display 12 of the portable information terminal 1 is relatively small in general. Therefore, when the image of waveform is increased in size by giving priority to visibility, the amount of information to be displayed is restricted, and when a large amount of biological information is displayed by giving priority to browsability, it is inevitable that sizes of respective information are reduced. However, browsability is secured as a desired amount of biological information is displayed on the display 12 according to the above configuration. When a point requiring more detailed check is subsequently designated, the trimmed image T including image information of that point alone is independently displayed, therefore, the line of sight of the user including a subject himself/herself and a medical stuff is introduced into the trimmed image T, which makes close observation easier. Accordingly, work of checking information by the user can be assisted in the case where biological information is displayed in the relatively small display area of the portable information terminal 1.

In the shown example, the trimmed image is displayed so as to be superimposed on the waveforms originally displayed on the display 12. That is, portions where importance of the check is relatively low in the waveforms originally displayed on the display 12 are covered with the trimmed image T.

According to the above structure, it is possible to introduce the line of sight to the trimmed image T more easily while utilizing the limited display area of the display 12 at the maximum.

Figure 5A:
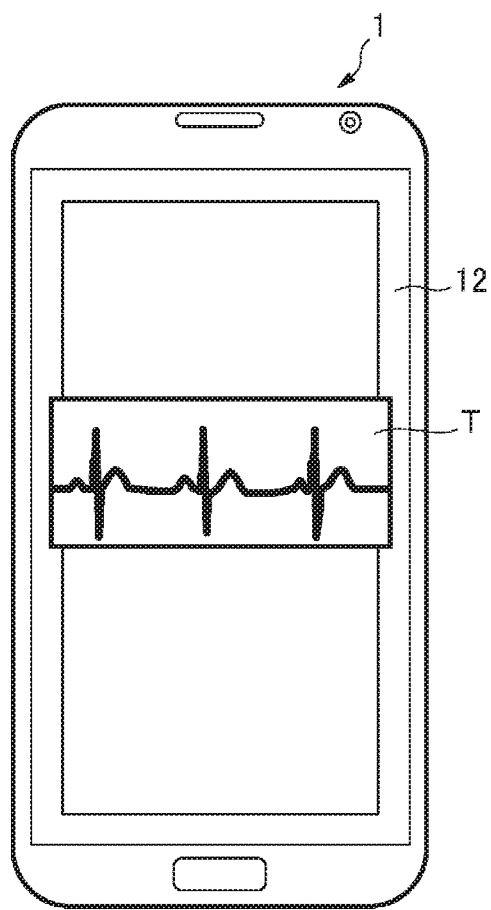
FIGS. 5A and 5B show display examples on the display of the above portable information terminal.
Figure 5B:
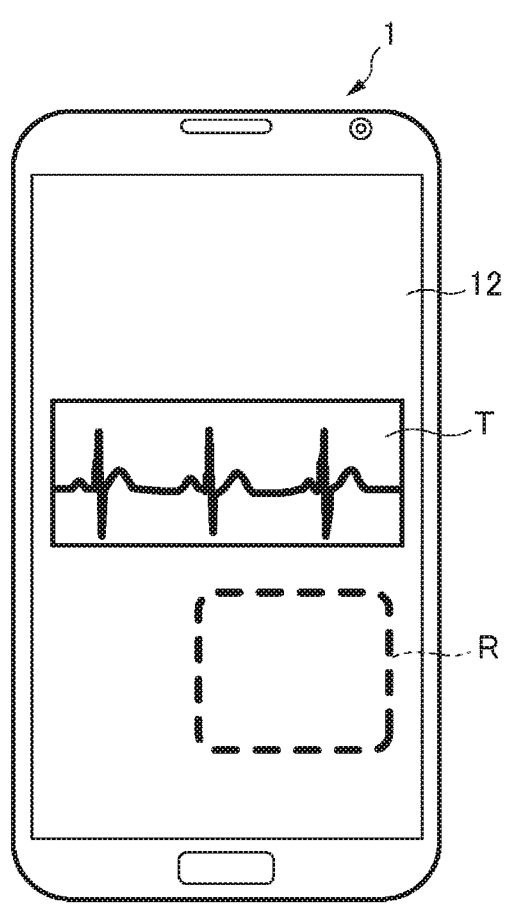

In this case, visibility of waveforms positioned behind the trimmed image T may be reduced as shown in FIG. 5A. The reduction of visibility can be realized by image processing such as gray-out of a screen including waveforms or off-focusing of the waveform image. The waveforms originally displayed on the display 12 may be completely deleted as shown in FIG. 5B.

According to the above configuration, the attention to image information inside the trimmed image T can be increased more.

The trimmed image T may contain an enlarged image of the designated part of the waveform as in respective shown example.

According to the above configuration, more detailed information concerning the designated part of the waveform can be obtained.

Supplementary information of part of the waveform contained in the trimmed image T can be displayed in an area R surrounded by a broken line in FIG. 5B. The supplementary information means information other than the waveform recorded while being associated with the part of the waveform. As supplementary information, a name of a biological parameter relating to the waveform, characteristic measured values (the maximum value, the minimum value, an average value and so on), alarm information (deviation of measured values from a given range, judgement of arrhythmia and so on), measurement time information, event information associated with measurement time and so on can be cited as examples.

According to the above configuration, more information which can assist the check of information by the user can be provided while utilizing the limited display area on the display 12 at the maximum.

In the example shown in FIGS. 4A and 4B, a given operation received by the user interface 13 for displaying the trimmed image T by designating part of the waveform is a pinch-out operation performed with respect to the touch panel device.

According to the configuration, part of biological information originally displayed on the display 12 can be designated intuitively and easily. Therefore, the work of checking information by the user can be assisted in the case where a large amount of biological information is displayed in the relatively small display area of the portable information terminal 1.

The above biological information management method is realized by executing a biological information management program by a processor of the portable information terminal 1. The program may be previously installed in a memory working with the processor as well as may be read out from a storage medium storing the program. Such storage medium may be provided as a portable storage medium such as a SD card or a USB memory as well as may be a storage medium included by a server device to which the portable information terminal 1 can be connected through a communication network.

The above embodiment is just an exemplification for making the present invention easy to understand. The configurations relating to the above embodiment can be suitably altered and improved within a scope not departing from the gist of the present invention.

In order to achieve the above object, a portable information terminal according to an embodiment includes a wireless communication device receiving sensor signals corresponding to biological information of a subject, a display displaying waveforms indicating variations with time in biological information of the subject based on the sensor signals, and a user interface receiving a given operation, in which, when part of the waveform is designated by the given operation, a trimmed image of the part of the waveform is displayed on the display.

Also in order to achieve the above object, a biological information management method according to an embodiment is executed by a processor in a biological information management system including sensors wirelessly transmitting sensor signals corresponding to biological information of a subject and a portable information terminal provided with the processor and receiving the sensor signals, which includes the steps of displaying waveforms indicating variations with time in biological information of the subject on a display of the portable information terminal based on the sensor signals and, when part of the waveform is designated through a user interface of the portable information terminal, displaying a trimmed image of the part of the waveform on the display.

The display of the portable information terminal is relatively small in general. Therefore, when the image of waveforms is increased in size by giving priority to visibility, the amount of information to be displayed is restricted, and when a large amount of biological information is displayed by giving priority to browsability, it is inevitable that sizes of respective information are reduced. However, browsability is secured as a desired amount of biological information is displayed on the display according to the above configuration. When a point requiring more detailed check is subsequently designated, the trimmed image including image information of that point alone is displayed, therefore, the line of sight of the user including a subject himself/herself and a medical stuff is introduced into the trimmed image, which makes close observation easier. Accordingly, work of checking information by the user can be assisted in the case where biological information is displayed in the relatively small display area of the portable information terminal.

As further another aspect for achieving the above object, there is proposed a biological information management program allowing the above biological information management method to be executed by a portable information terminal.

As further another aspect for achieving the above object, there is proposed a computer-readable storage medium storing the above biological information management program.

What is claimed is:
1. A portable information terminal comprising:
a wireless communication device configured to receive sensor signals corresponding to biological information of a subject;
a display configured to display waveforms indicating variations with time in biological information of the subject based on the sensor signals; and
a user interface configured to receive a given operation, wherein, when a part of one of the waveforms is designated by the given operation, a trimmed image of the part of the one of the waveforms is displayed on the display, and
a whole of the trimmed image is opaque, wherein when the trimmed image of the part of the one of the waveforms is generated, other ones of the waveforms behind the trimmed image are hidden.

2. The portable information terminal according to claim 1, wherein the trimmed image is displayed so as to be superimposed on the waveforms.

3. The portable information terminal according to claim 1, wherein the trimmed image includes an enlarged image of the part of the one of the waveforms.

4. The portable information terminal according to claim 1, wherein supplementary information of the part of the waveform is displayed on the display with the trimmed image.

5. The portable information terminal according to claim 1, wherein the user interface is a touch panel device allowing touch input with respect to the display, and
the given operation is a pinch-out operation.

6. The portable information terminal according to claim 1, wherein a visibility of other parts of the one of the waveforms that are not designated is reduced.

7. The portable information terminal according to claim 1, wherein at least a part of display data of the other ones of the waveforms behind the trimmed image is deleted.

8. The portable information terminal according to claim 4, wherein the supplementary information includes at least one of characteristic measured values, alarm information, and event information associated with the measurement time, wherein the characteristic measured values are numerical, and wherein the supplementary information is displayed, on the display, in conjunction with the trimmed image.

9. A biological information management method executed by a processor in a biological information management system including sensors wirelessly transmitting sensor signals corresponding to biological information of a subject and a portable information terminal provided with the processor and receiving the sensor signals, the method comprising the steps of:
displaying waveforms indicating variations with time in biological information of the subject on a display of the portable information terminal based on the sensor signals; and
when a part of one of the waveforms is designated through a user interface of the portable information terminal, displaying a trimmed image of the part of the one of the waveforms on the display, and
a whole of the trimmed image is opaque, wherein when the trimmed image of the part of the one of the waveforms is generated, other ones of the waveforms behind the trimmed image are hidden.

10. The biological information management method according to claim 9, wherein a visibility of other parts of the one of the waveforms that are not designated is reduced.

11. The biological information management method according to claim 9, further comprising:
displaying, after the trimmed image is displayed, supplementary information of the part of the waveform on the display in conjunction with the trimmed image, wherein the supplementary information includes at least one of a name of biological information relating to the waveforms, characteristic measured values, alarm information and event information associated with measurement time, wherein the characteristic measured values are numerical.

12. A computer-readable storage medium storing a biological information management program configured to cause a processor in a biological information management system including sensors wirelessly transmitting sensor signals corresponding to biological information of a subject and a portable information terminal provided with the processor and receiving the sensor signals, to perform operations comprising:

displaying waveforms indicating variations with time in biological information of the subject on a display of the portable information terminal based on the sensor signals; and when a part of one of the waveforms is designated through a user interface of the portable information terminal, displaying a trimmed image of the part of the one of the waveforms on the display, and a whole of the trimmed image is opaque, wherein when the trimmed image of the part of the one of the waveforms is generated, other ones of the waveforms behind the trimmed image are hidden.

13. The computer-readable storage medium according to claim 12, wherein a visibility of other parts of the one of the waveforms that are not designated is reduced.

14. The computer-readable storage medium according to claim 12, wherein the operations further comprises displaying, after the trimmed image is displayed, supplementary information of the part of the waveform on the display in conjunction with the trimmed image, wherein the supplementary information includes at least one of a name of biological information relating to the waveforms, characteristic measured values, alarm information and event information associated with measurement time, wherein the characteristic measured values are numerical.

15. A portable information terminal comprising:

a wireless communication device configured to receive sensor signals corresponding to biological information of a subject;

a display configured to display waveforms indicating variations with time in biological information of the subject based on the sensor signals; and a user interface configured to receive a given operation, wherein, when a part of one of the waveforms is designated by the given operation, a trimmed image of the part of the one of the waveforms is displayed on the display, a whole of the trimmed image is opaque, wherein when the trimmed image of the part of the one of the waveforms is generated, other ones of the waveforms behind the trimmed image are hidden, wherein supplementary information of the part of the waveform is displayed on the display with the trimmed image, and wherein the supplementary information includes at least one of characteristic measured values, alarm information, and event information associated with measurement time, wherein the characteristic measured values are numerical.

16. The portable information terminal according to claim 15, wherein the supplementary information is generated after the part of the one of the waveforms is designated to be displayed in conjunction with the trimmed image.

* * * * *